(12) United States Patent
Nakata

(10) Patent No.: US 6,916,288 B2
(45) Date of Patent: Jul. 12, 2005

(54) METHOD FOR THE SKIN ANALYSIS

(76) Inventor: Yasutaka Nakata, Grandsocie Kunitachi West 811, 41-1, Fujimidai 4-chome, Kunitachi-shi, Tokyo (JP), 186-0003

( * ) Notice: Subject to any disclaimer, the term of this patent is extended or adjusted under 35 U.S.C. 154(b) by 230 days.

(21) Appl. No.: 10/365,539

(22) Filed: Feb. 13, 2003

(65) Prior Publication Data
US 2004/0122299 A1 Jun. 24, 2004

(30) Foreign Application Priority Data
Dec. 24, 2002 (JP) .......................................... 2002-372682

(51) Int. Cl.⁷ ................................................. A61B 5/00
(52) U.S. Cl. ...................................................... 600/306
(58) Field of Search ............................... 600/306, 300, 600/309

(56) References Cited

U.S. PATENT DOCUMENTS 5,836,872 A * 11/1998 Kenet et al. ................. 600/306
5,938,593 A * 8/1999 Ouellette ..................... 600/300
6,208,749 B1 * 3/2001 Gutkowicz-Krusin et al. ... 382/128
6,790,179 B2 * 9/2004 Skover ........................ 600/306
2002/0016539 A1 * 2/2002 Michaelis et al. ........... 600/407

* cited by examiner

Primary Examiner—Robert L. Nasser
Assistant Examiner—Navin Natnithithadha
(74) Attorney, Agent, or Firm—Wenderoth, Lind & Ponack, L.L.P.

(57) ABSTRACT

The method for the skin analysis is capable of deciding condition of the skin of the customer objectively and accurately. There are obtained analysis data of the skin of the customer based on a plurality of the skin analysis techniques such as the skin analysis according to diagnostic process with an interview, analysis of the skin according to replica of the skin using impression agent, information analysis within keratin by keratin checker, melanin information analysis by melanin checker, flesh color analysis based on flesh color sheet. There is classified conditions of the skin of the customer in every plural categories based on the analysis data of this skin, and then the condition of the skin of the customer is made to analyze in accordance with classification obtained.

6 Claims, 14 Drawing Sheets

FIG. 3

KIND OF FOUNDATION

IN ORDER TO SELECT CLEANSING AGENT, IT IS IMPORTANT WHETHER OR NOT THERE IS USED PREARRANGEMENT, AND IT IS IMPORTANT WHAT TYPE OF FOUNDATION IS USED. SELECT ONE WHETHER OR NOT PREARRANGEMENTS IS USED. SELECT APPROPRIATE ONE OF WHICH ARE KIND OF FOUNDATION AND COMBINATION THEREOF IN USE AT THE PRESENT DAY.

| No. | USE OF PREARRANGEMENTS |
|---|---|
| 1 | NO USE OF PREARRANGEMENTS |
| 2 | IN USE OF PREARRANGEMENTS |

| No. | KIND AND COMBINATION OF FOUNDATION IN USE |
|---|---|
| 1 | NO MAKEUP |
| 2 | ONLY POINT MAKEUP |
| 3 | USE ONLY POWDERY FOUNDATION OR BREAST POWDER |
| 4 | USE ONLY 2-WAY FOUNDATION (USE BY SPONGE WITH WATER) |
| 5 | USE ONLY 2-WAY FOUNDATION (USE BY DRY SPONGE) |
| 6 | USE ONLY FACE POWDER WITH WATER |
| 7 | USE BREAST BOWDER ON FACE POWDER WITH WATER |
| 8 | USE ONLY LIQUID FOUNDATION |
| 9 | USE POWDER (POWDERY, BREAST POWDER) ON LIQUID FOUNDATION |
| 10 | USE ONLY CREAM FOUNDATION |
| 11 | USE POWDER (POWDERY, BREAST POWDER) ON CREAM FOUNDATION |

FIG.4

DEGREE OF HEALTH OF THE SKIN

IN CASES WHERE THERE IS PERFORMED CARE OF THE SKIN, TO KNOW DEGREE OF HEALTH OF THE SKIN IS IMPORTANT FOR THE MATTER TO HIGHTEN EFFECT OF CARE AS WELL AS TO PREVENT TROUBLE PREVIOUSLY. ANSWER THE QUESTION WITH RESPECT TO CONDITION WITHIN 2, OR 3 WEEKS. ANSWER "YES" WHEN CONDITION CORRESPOND TO WHOLE CONTENT OF QUESTION, WHILE ANSWER "NO" WITH THE EXCEPTION THEREOF.

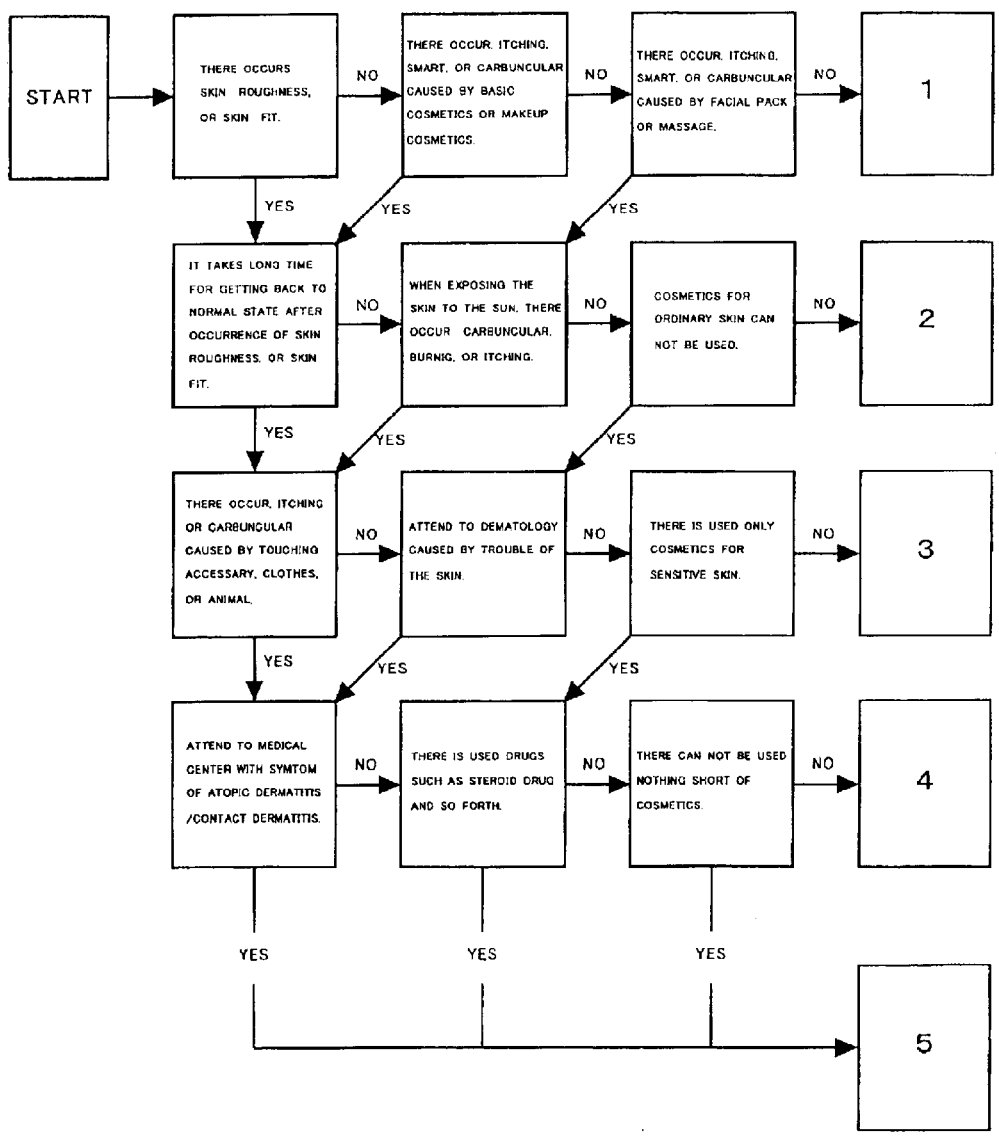

FIG.5

BALANCE BETWEEN MOISTURE / FAT COMPONENTS OF THE SKIN

BALANCE BETWEEN MOISTURE / FAT COMPONENTS OF THE SKIN PRESENTS WHETHER OR NOT PHYSIOLOGY OF THE SKIN OPERATES SMOOTHLY. DO MAINTENANCE WITH COSMETICS BEST SUITED FOR THE CONDITION OF THE SKIN WHILE CHECKING DILIGENTLY THE CONDITION OF THE SKIN ON A DAY-TO-DAY BASIS. <u>ANSWER THE QUESTION WITH RESPECT TO CONDITION WITHIN 2, OR 3 WEEKS. ANSWER "YES" WHEN CONDITION CORRESPOND TO WHOLE CONTENT OF QUESTION, WHILE ANSWER "NO" WITH THE EXCEPTION THEREOF.</u>

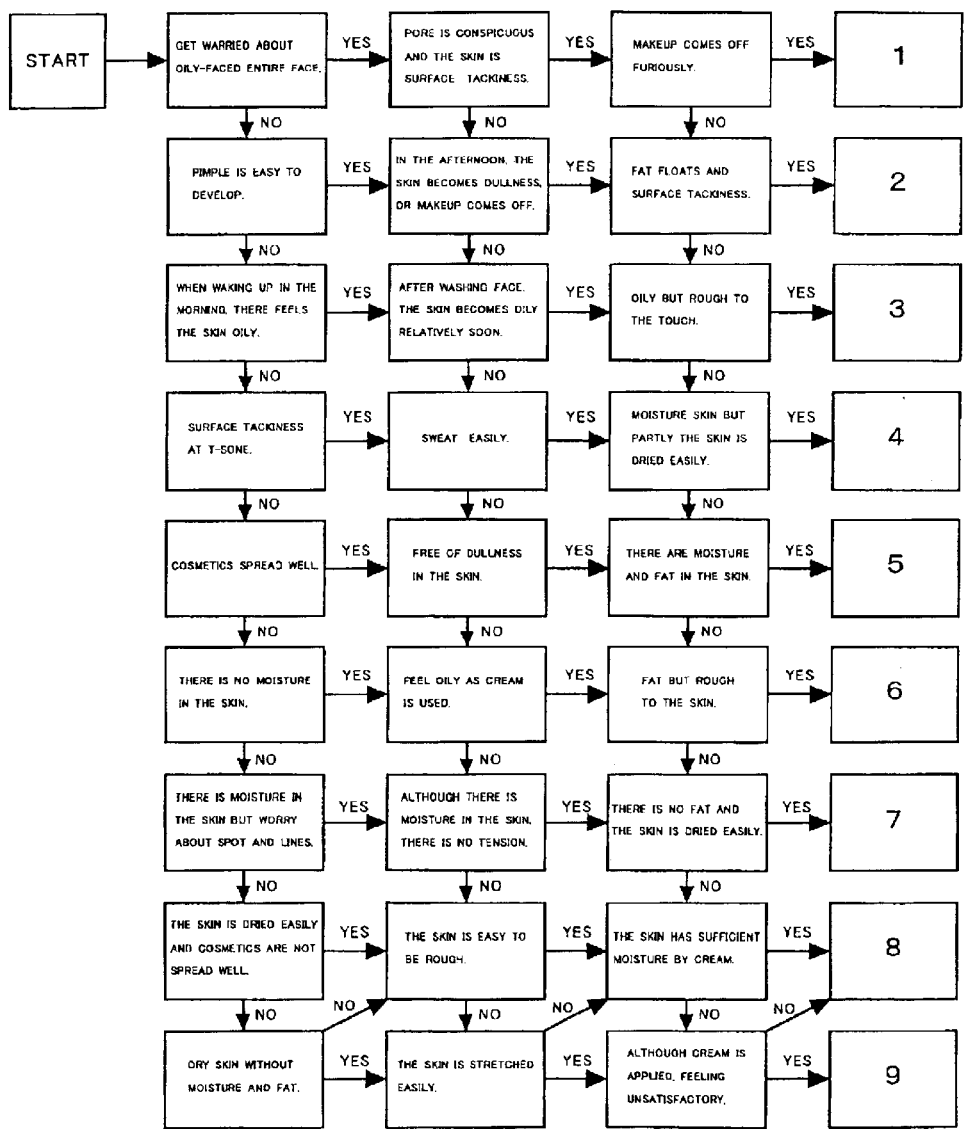

FIG. 6

SKIN TROUBLE

METHOD FOR GETTING RID OF SKIN TROUBLE BECOMES POSSIBLE ONLY AFTER PERFORMING MAINTENANCE CORRESPONDING TO TROUBLE WHILE BEING WELL AWARE OF OWN CONSTITUTION, PHYSICAL CONDITION, CONDITION OF THE SKIN, THE NATURE OF THE SKIN AND CONDITION OF TROUBLE. SELECT EACH ONE NUMBER OF WORRY OF THE SKIN THAT YOU FEEL WORST WORRY, AND WHEN THE WORRY OCCURS.

| No | THE WORST WORRY OF THE SKIN | PERIOD OF TIME | |
|---|---|---|---|
| 1 | NO TROUBLE ON THE SKIN | (0) | |
| 2 | DRY SKIN IS EASY TO OCCUR | (1) HAD BEEN WORRIED ALWAYS | (2) BE WORRIED RECENTLY |
| 3 | ROUGH TO THE SKIN | (3) HAD BEEN WORRIED ALWAYS | (4) BE WORRIED RECENTLY |
| 4 | SKIN IS STRETCHED AFTER WASHING FACE | (5) HAD BEEN WORRIED ALWAYS | (6) BE WORRIED RECENTLY |
| 5 | SKIN BECOMES ROUGH | (7) HAD BEEN WORRIED ALWAYS | (8) BE WORRIED RECENTLY |
| 6 | SKIN IS OILY | (9) HAD BEEN WORRIED ALWAYS | (10) BE WORRIED RECENTLY |
| 7 | MAKEUP COMES OFF EASILY | (11) HAD BEEN WORRIED ALWAYS | (12) BE WORRIED RECENTLY |
| 8 | GET WORRIED ABOUT PIMPLE | (13) HAD BEEN WORRIED ALWAYS | (14) BE WORRIED RECENTLY |
| 9 | GET WORRIED ABOUT INFLAMMATORY PIMPLE | (15) HAD BEEN WORRIED ALWAYS | (16) BE WORRIED RECENTLY |
| 10 | GET WORRIED ABOUT WHITE PIMPLE | (17) HAD BEEN WORRIED ALWAYS | (18) BE WORRIED RECENTLY |
| 11 | GET WORRIED ABOUT BLACK PIMPLE | (19) HAD BEEN WORRIED ALWAYS | (20) BE WORRIED RECENTLY |
| 12 | GET WORRIED ABOUT TRACES OF PIMPLE | (21) HAD BEEN WORRIED ALWAYS | (22) BE WORRIED RECENTLY |
| 13 | GET WORRIED ABOUT PORE | (23) HAD BEEN WORRIED ALWAYS | (24) BE WORRIED RECENTLY |
| 14 | MIXED SKIN | (25) HAD BEEN WORRIED ALWAYS | (26) BE WORRIED RECENTLY |
| 15 | GET WORRIED ABOUT FREKLE | (27) HAD BEEN WORRIED ALWAYS | (28) BE WORRIED RECENTLY |
| 16 | GET WORRIED ABOUT SPOTS | (29) HAD BEEN WORRIED ALWAYS | (30) BE WORRIED RECENTLY |
| 17 | GET WORRIED ABOUT FINE WRINKLES | (31) HAD BEEN WORRIED ALWAYS | (32) BE WORRIED RECENTLY |
| 18 | GET WORRIED ABOUT LINES | (33) HAD BEEN WORRIED ALWAYS | (34) BE WORRIED RECENTLY |
| 19 | GET WORRIED ABOUT BAGS | (35) HAD BEEN WORRIED ALWAYS | (36) BE WORRIED RECENTLY |
| 20 | NO TENSION ON THE SKIN | (37) HAD BEEN WORRIED ALWAYS | (38) BE WORRIED RECENTLY |
| 21 | COSMETICS ARE NOT SPREAD | (39) HAD BEEN WORRIED ALWAYS | (40) BE WORRIED RECENTLY |
| 22 | FOREHEAD IS YELLOW | (41) HAD BEEN WORRIED ALWAYS | (42) BE WORRIED RECENTLY |
| 23 | CHEEK IS RED | (43) HAD BEEN WORRIED ALWAYS | (44) BE WORRIED RECENTLY |
| 24 | DULNESS ON THE SKIN | (45) HAD BEEN WORRIED ALWAYS | (46) BE WORRIED RECENTLY |
| 25 | CAPILLARY IS DISTINDED AND FLOATED | (47) HAD BEEN WORRIED ALWAYS | (48) BE WORRIED RECENTLY |
| 26 | SUNBURN | (49) GET WORRIED ABOUT SUNBURN | |
| 27 | SKIN IS SMARTED WHEN CHANGING COSMETICS | (50) HAD BEEN WORRIED ALWAYS | (51) BE WORRIED RECENTLY |
| 28 | SKIN IS CARBUNCULAR | (52) HAD BEEN WORRIED ALWAYS | (53) BE WORRIED RECENTLY |
| 29 | SOMETIMES EXPERIENCE ITCHING | (54) HAD BEEN WORRIED ALWAYS | (55) BE WORRIED RECENTLY |
| 30 | SOMETIMES SKIN IS CARBUNCULAR | (56) HAD BEEN WORRIED ALWAYS | (57) BE WORRIED RECENTLY |

FIG. 7

CHECK CORRESPONDING MATTERS ABOUT NEXT QUESTIONS

| | | |
|---|---|---|
| HEALTH CONDITIONS | PHYSICAL CONDITION | ☐ IN GOOD CONDITION ☐ IN BAD CONDITION |
| | ALLEGY | ☐ NO ☐ YES |
| | TIREDNESS | PHYSICALLY: ☐ UTTERLY FATIGUED ☐ EASY TO FATIGUE ☐ HARDLY NO PSYCHOLOGICALLY: ☐ STABLE ☐ UNSTABLE (WORRY, IRRITITATED, ATTENTIVE) |
| | MENSTRUATION | ☐ FAVORABLE ACCOUNT ☐ MENSTRUAL DISORDER |
| | MEDICALS IN COMMON USE | ☐ NO ☐ YES ( ) |
| LIVING CONDITIONS | LIVING | ☐ REGULAR ☐ IRREGULAR |
| | EXERCISE | ☐ SOMETIMES ☐ NO |
| DIET | DIET MEAL | ☐ REGULAR ☐ IRREGULAR |
| | FOOD TENDENCY | ☐ JAPANESE COOKING ☐ WESTERN COOKING ☐ CHINESE COOKING |
| | TASTE TENDENCY | ☐ BLAND ☐ HIGHLY SEASONED |
| CONDITIONS OF THE SKIN | CHARACTERISTIC | ☐ PIMPLE ☐ TRACES OF PIMPLE ☐ SPOT ☐ LINES ☐ DISTINDED CAPILLARY ☐ MULTI-DOWNY HAIR ☐ ALLEGY |
| | COLOR OF FACE | ☐ HIGH COMPLEXION ☐ PALE COMPLEXION ☐ YELLOWISH FACE ☐ SWARTHY FACE |
| | LUSTRE OF SKIN | ☐ GOOD ☐ AVARAGE ☐ BAD |
| | THICKNESS OF SKIN | ☐ THICK ☐ AVERAGE ☐ THIN |
| | TENSION OF SKIN | ☐ YES ☐ AVERAGE ☐ NO ☐ PARTLY ☐ WIDELY |
| | LINES OF SKIN | ☐ MANY ☐ A FEW ☐ SUPERFICIAL ☐ DEEP ☐ PARTLY ☐ WIDELY |
| | SPOT OF SKIN | ☐ YES ☐ NO ☐ A FEW ☐ PARTLY ☐ WIDELY ☐ BLACK ☐ BROWN ☐ LIVER ☐ BEIGE |
| | SPREAD OF COSMETICS | ☐ GOOD ☐ AVERAGE ☐ NOT VERY GOOD ☐ NO GOOD |
| | DEFORMATION OF MAKEUP | ☐ NO ☐ SIMPLY ☐ PARTLY (☐ FOREHEAD ☐ NODE ☐ CHEEK ☐ ARROUD MOUTH) |
| | SKIN FIT | ☐ NO ☐ YES EASY ☐ BASIC COSMETICS ☐ MAKEUP ☐ HAIR CARE |
| | PIMPLE | ☐ OCCASIONALLY ☐ OFTEN ☐ HARDLY |
| | SENSITIVE TO THE SUN | ☐ INFLAMMATION WITH HEAT ☐ RED BEFORE BLACK ☐ DRY SKIN |
| | SECRETION OF SWEAT | ☐ MUCH ☐ AVERAGE ☐ LITTLE |
| | SKIN TEPERATURE | ☐ HIGH ☐ AVERAGE ☐ LOW ☐ GOOD BALANCE ☐ NO GOOD BALANCE |
| | SKIN MOISTURE | ☐ MUCH ☐ AVERAGE ☐ LITTLE ☐ GOOD BALANCE ☐ NO GOOD BALANCE |
| | SKIN FAT | ☐ MUCH ☐ AVERAGE ☐ LITTLE ☐ GOOD BALANCE ☐ NO GOOD BALANCE |
| | SKIN Ph | ☐ SLIGHTLY ACIDIC ☐ NORMAL ☐ SLIGHTLY ALKALINE |
| | EVAPORATIVITY OF MOISTURE | ☐ HIGH ☐ AVERAGE ☐ LOW |
| THE OTHERS | NECK | ☐ LINES ☐ TWOFOLD CHIN ☐ BAGS ☐ DULNESS |
| | HAIR CHARACTERISTIC | ☐ DRY ☐ MOISTURE ☐ OILY ☐ DAMAGED ☐ NORMAL ☐ COMBING |
| | NAIL CHARACTERISTIC | ☐ LUSTRE ☐ AVERAGE ☐ NO LUSTTRE |

| ATOPIC DERMATICIS ALLEGY SKIN | SENSITIVE SKIN | SLIGHTLY SENSITIVE SKIN | SLIGHTLY UNSTABLE SKIN | HEALTHY SKIN |
|---|---|---|---|---|
| 1 | 2 | 3 | 4 | 5 |

FIG.12
SKIN CLASSIFICATION (KERATIN)
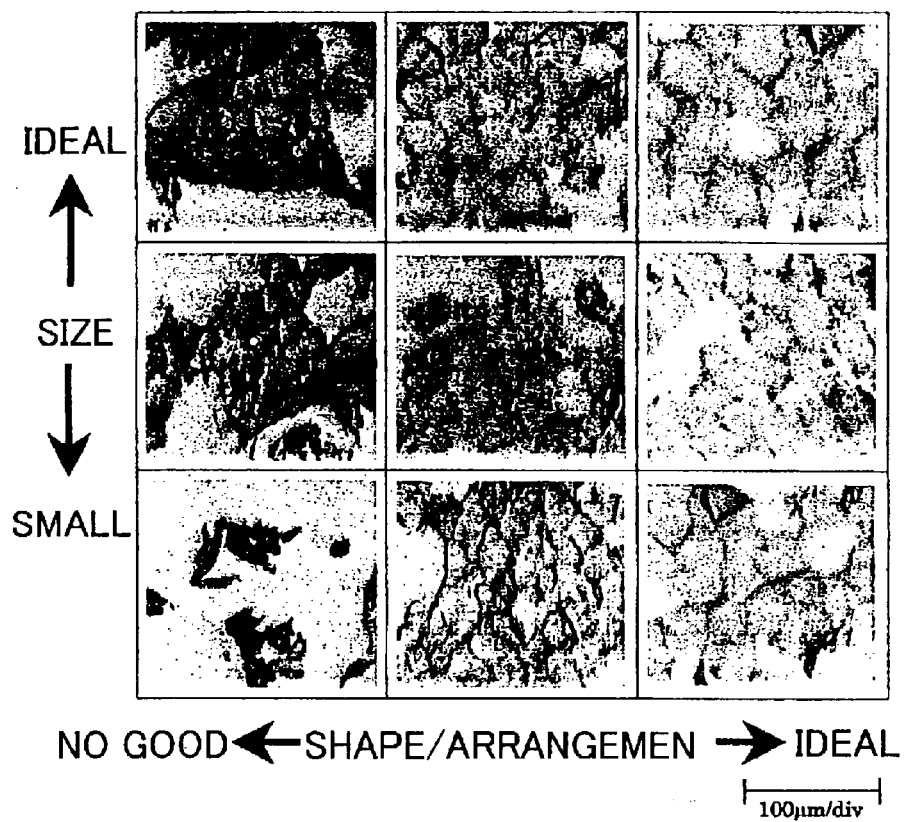
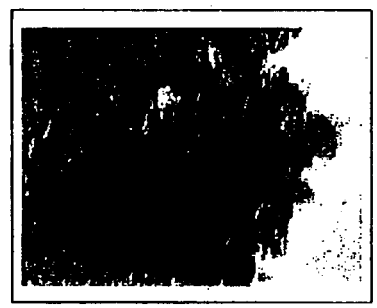
THERE IS FOUND A NUCLEUS.

METHOD FOR THE SKIN ANALYSIS

CROSS REFERENCE TO RELATED APPLICATIONS

This application is related to Japanese Patent Application No. 2002-372682 filed on Dec. 24, 2002, based on which this application claims priority under the Paris Convention and contents of which are incorporated herein by reference.

BACKGROUND OF THE INVENTION

1. Field of the Invention

The present invention relates to methods for the skin analysis, more particularly, to methods for the skin analysis used for cosmetics selling system.

2. Description of the Related Art

Originally, the skin of a human being vary in accordance with age, physical condition, physical constitution, change of the seasons or so forth. Thus, on a case-by-case basis, it is necessary for the customer to diagnose details of the skin precisely in conformity with condition of the skin or condition of the trouble occurring on the skin. The most appropriate condition of the skin for the customer can be obtained only after performing selection of cosmetics or selection of maintenance procedure of the skin based on this diagnosis.

Conventionally, in cases where there are selected the cosmetics for the particular customer to provide, in the greater number of cases, the cosmetics are selected according to sensuous decision of the customer or subjectivity of cosmetic sales people, accordingly, selected cosmetics are not always optimum for the skin of the customer. For that reason, as matters now stand, the customers change cosmetics successively, in order to look around for the cosmetics suitable for oneself over lifetime. Further, conventional diagnosis of the skin of the customer is one in which conditions of the skin are made to separate into at most degrees of four or five kinds to discriminate. Therefore, conventional diagnosis of the skin for the customer can not catch perfectly characteristic of the skin of the customer.

In order to resolve these problems, the method has been disclosed in the Japanese Patent Application Laid-Open No. 2002-269212, in which questions with respect to the conditions of the skin of the customer and the nature of the skin of the customer are made to put to the customer, then diagnosis of the skin is performed based on answers from the customers and then support of the makeup is executed. In addition, the method has been disclosed in the Japanese Patent Application Laid-Open No. 2001-104050 in which support of the makeup is executed while referring to knowledge database after analyzing face image incorporated in the camera. However these methods are incomplete ones. Furthermore, the system of the skin analysis which uses replica of the skin or also keratinous cell piece has been disclosed in the Japanese Patent Application Laid-Open No. 2002-65616, however, its analysis method is not too concrete.

As described above, in the way of the conventional method of the skin analysis for adding objectivity to the selection of the cosmetics, the method according to the diagnostic process with an interview or analysis of the face image have been reported, however, these are not complete, and there is no sufficient objectivity.

SUMMARY OF THE INVENTION

It is an object of the present invention to provide a method for skin analysis in which the condition of the skin of the customer is made to diagnose as objective as possible and precisely while resolving above described problems.

According to a first aspect of the present invention, there is provided a method for analyzing the skin, the method comprising the steps of analyzing the skin to obtain analysis data of the skin of the customer based on a plurality of the skin analysis technique, classifying conditions of the skin of the customer into a plurality of classifications in every respective categories based on the skin analysis data obtained by this skin analysis step, and diagnosing the skin condition to diagnose condition of the skin of the customer in accordance with the classifications obtained by said classification step, Wherein the diagnosis of the skin analysis is performed via the above-described respective steps.

By this method, there can be classified conditions of the skin relatively easy way and accurately from a plurality of points of view, and it is possible to realize the method for the skin analysis capable of diagnosing and analyzing endowments and conditions of the skin.

According to a second aspect of the present invention, there is provided the method for analyzing the skin, wherein diagnosis result of the skin based on answers of the diagnostic process with an interview concerning condition of the skin, the nature of the skin and current maintenance procedure in terms of the customer is included as one of the plurality of the skin analysis techniques.

By this method, it is possible to know in detail conditions of the skin of the customer, the nature of the skin and the conventional circumstances of maintenance procedure and so forth together with subjective decision of the customer, and it is possible to classify characteristic of the skin for individual person based thereupon, thus it is possible to indicate concrete advise or selection method of cosmetics appropriate to an individual.

According to a third aspect of the present invention, there is provided the method for analyzing the skin wherein decision result according to image analysis of replica by impression agent in which irregularities of surface of the skin is copied is included as one of said plurality of the skin analysis techniques.

By this method, it is possible to classify in detail condition of the skin based on texture, tension, pore, flow of skin groove, existence of trouble, kind of trouble and so forth, and it is possible to indicate concrete advise or selection method of cosmetics appropriate for an individual.

According to a fourth aspect of the invention, there is provided the method for analyzing the skin wherein analysis of information data within the keratin by a keratin checker for discriminating keratin component obtained from the skin of the customer is included as one of the plurality of the skin analysis techniques.

By this method, it is possible to classify objectively characteristic of the skin of an individual while recognizing moisture of the cell or health condition upon checking shape, size and arranged condition of the cell within the keratin of the skin, thus it is possible to indicate concrete advise or selection method of cosmetics appropriate for an individual based thereon.

According to a fifth aspect of the present invention, there is provided the method for analyzing the skin wherein analysis of information data of melanin by a melanin checker for deciding condition of pigment of the skin is included as one of said plurality of the skin analysis techniques.

By this method, health condition of the skin on the melanin is made to recognize while checking amount of melanin component of the skin and dispersion of melanin components and so forth, thus it is possible to indicate concrete advise or selection method of cosmetics appropriate for an individual based thereon.

According to a sixth aspect of the present invention, there is provided the method for analyzing the skin wherein analysis of decision data of flesh color based on flesh color sheet is included as one of the plurality of the skin analysis techniques.

By this method, there is analyzed flesh color of the customer, so that it is possible to indicate concrete advise or selection method of cosmetics appropriate for an individual based thereon.

According to a seventh aspect of the present invention, there is provided the method for analyzing the skin wherein the classification step is predicated on the tree shaped classifications based on categories such as condition of the skin, the nature of the skin, the texture of the skin, surface waviness of the skin, pore, direction of flow of groove, existence of trouble, health condition, current busy condition of cosmetics or so forth.

By this method, it is possible to execute classification of the skin based on the category easily and relatively short time.

According to an eighth aspect of the present invention, there is provided the method for analyzing the skin wherein the classification step is predicated on pattern matching image processing in terms of database sample of replica on which irregularity of surface of the skin is copied.

By this method, it is possible to execute classification of the skin in relatively short time and accurately while using the computer.

Other and further objects and features of the present invention will be become obvious upon understanding of the illustrative embodiments about to be described in connection with the accompanying drawings or will be indicated in the appended claims, and various advantages not referred to herein will occur to one skilled in the art upon employing of the invention in practice.

BRIEF DESCRIPTION OF THE DRAWINGS

FIG. 3 is a diagram illustrating an exemplary questionnaire of question in terms of prearrangements, foundation cosmetics.

FIG. 4 is a diagram illustrating an exemplary questionnaire of question in terms of degree of health of the skin.

FIG. 5 is a diagram illustrating an exemplary questionnaire of question concerning balance between moisture/fat components of the skin.

FIG. 6 is a diagram illustrating an exemplary questionnaire of question concerning trouble about the skin in the past, and trouble about the skin at the present day.

FIG. 7 is a diagram illustrating an exemplary questionnaire of question concerning current health condition.

FIG. 12 is a diagram illustrating an exemplary result of decision of the skin in accordance with keratin analysis.

DETAILED DESCRIPTION OF THE PREFERRED EMBODIMENTS

Figure 1:
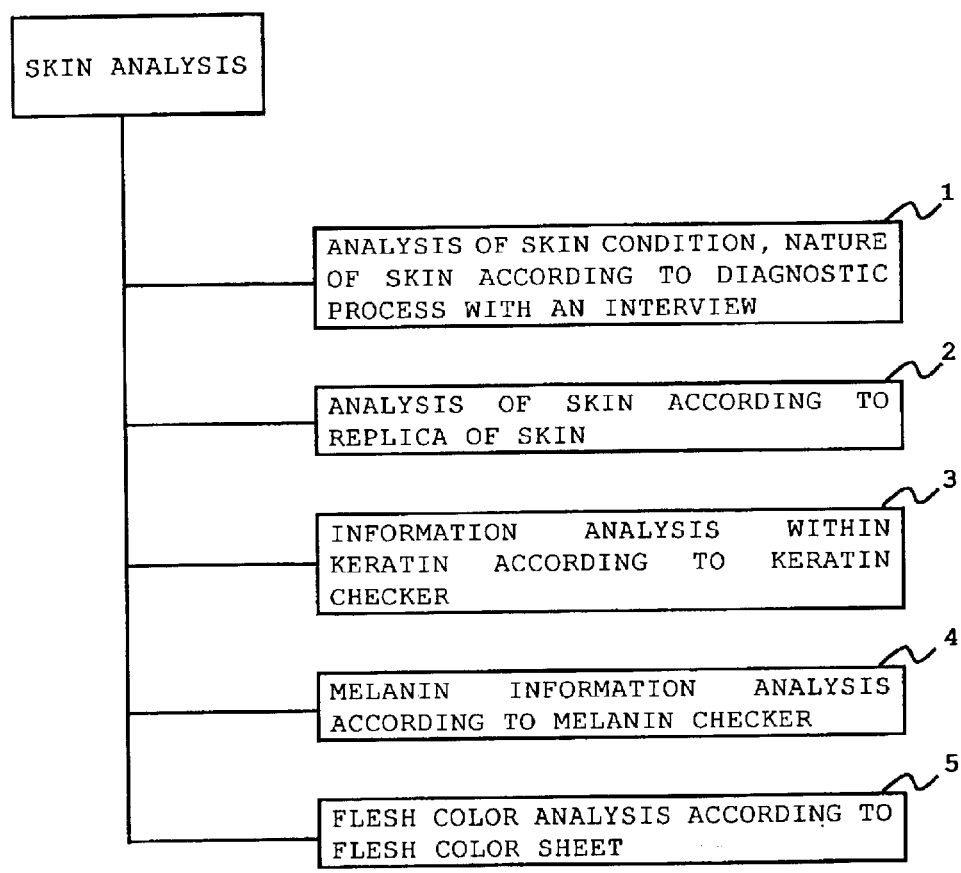
FIG. 1 is an explanation diagram illustrating method for skin analysis according to the present invention.

Various embodiments of the present invention will be described with reference to the accompanying drawings. It is to be noted that the same or similar reference numerals are applied to the same or similar parts and elements throughout the drawings, and the description of the same or similar parts and elements will be omitted or simplified.

The method for the skin analysis of the present invention can analyzes the skin of the customer with good precision based on information of health condition and so forth in accordance with diagnostic process with an interview, analysis result of the skin using replica of the skin, information data within keratin using keratin checker, information data of melanin using melanin checker, flesh color data based on flesh color sheet and season information or so forth. Selection of the optimum cosmetics for the customer is performed based on the result. Presentation of information concerning care of the skin to be performed hereafter in terms of the customer, esthetic program or makeup simulation are performed based on the result.

In the first instance, the method for skin analysis according to the present invention will be described in detail with reference to accompanying drawings.

FIG. 1 is an explanation diagram indicating the method for skin analysis of the present invention.

The method for skin analysis of the present invention separates into the skin analysis according to the diagnostic process with an interview of symbol 1, the analysis of the skin according to replica of the skin using the impression agent of symbol 2, the information analysis within the keratin using the keratin checker of symbol 3, the information analysis of the melanin using the melanin checker of symbol 4, and the flash color analysis based on the flash color sheet of symbol 5.

It should be noted that there is no specified order particularly in its execution order of the analysis.

Figure 2:
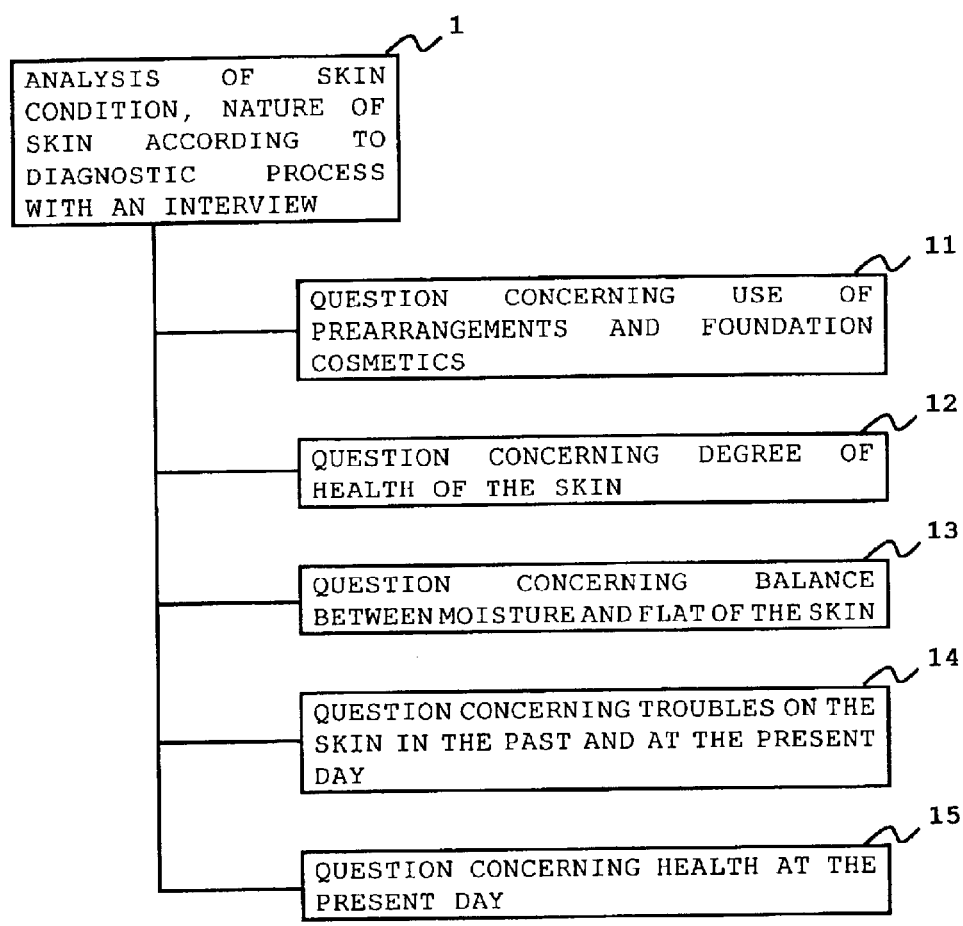
FIG. 2 is an explanation diagram illustrating content of the skin analysis according to the diagnostic process with an interview from among the methods for skin analysis of FIG. 1.

The skin analysis 1 according to the diagnostic process with an interview, for instance, as illustrated in FIG. 2, includes questions concerning prearrangements and foundation cosmetics of symbol 11, questions concerning degree of health of the skin of symbol 12, questions concerning balance between moisture/fat components of the skin of symbol 13, questions concerning troubles of the skin in the past and troubles of the skin at the present day of symbol 14, and questions concerning health at the present day of symbol 15.

The question 11 concerning prearrangements and foundation cosmetics from among these questions, for instance, in accordance with the questionnaire as illustrated in FIG. 3, investigates what type of prearrangements or foundation cosmetics is used currently. Also, the question 12 concerning degree of the health of the skin, for instance, in accordance with the questionnaire as illustrated in FIG. 4, investigates troubles such as skin roughness or skin fit generated within the last two or three weeks. The question 13 concerning balance between moisture/fat components of the skin, in accordance with the questionnaire as illustrated in FIG. 5, investigates moisture component of the skin (moisture of the skin), fat component of the skin (shiny of the skin) and so forth based on physiology of the skin within the last two or three weeks. The question 14 concerning troubles of the skin in the past and troubles of the skin at the present day, for instance, in accordance with the questionnaire as illustrated in FIG. 6, investigates worry of the skin about which the customer worries.

Also, the question 15 concerning the health at the present day, for instance, in accordance with the questionnaire as illustrated in FIG. 7, investigates condition of the health at the present day.

Figures 8A, 8B:
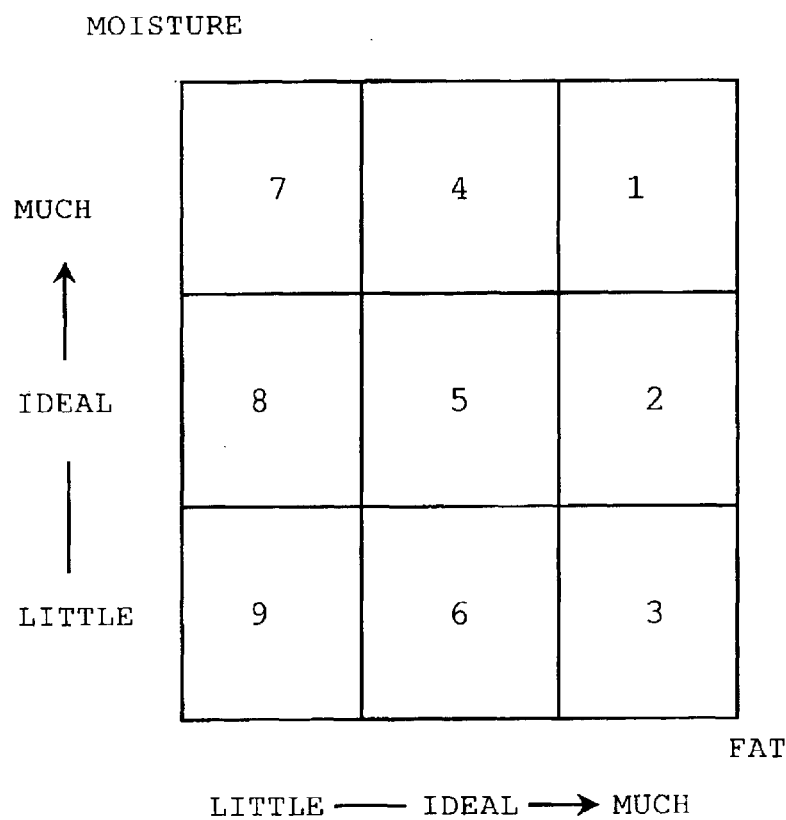
FIG. 8(A) is a classified diagram concerning health condition of the skin.
FIG. 8(B) is a classified diagram concerning the balance condition between moisture component and fat component.

It is possible to make certain that the condition of the skin at the present day corresponds to which position on the line of classification of FIG. 8(A) as a result of question of FIG. 4, for instance. Then, the customer is given guidance in ways of coping to improve the skin at the present day for the "healthy skin" of condition 5. It is also possible to make certain that the condition of the skin at the present day corresponds to which position on the plane of classification of FIG. 8(B) as an answer concerning question of FIG. 5. It is ideal that condition of the skin corresponds to the condition 5 on this plane, therefore, when the condition of the skin at the present day is classified into the conditions 1 to 4, or the conditions 6 to 9, the customer is given guidance in ways of coping to approach the skin at the present day for the "healthy skin" of condition 5.

These questions are, first and foremost, exemplary questions, and it is possible to diagnose fundamental conditions such as characteristic and/or degree of health for the skin of the customer from the answers in terms of such a series of questions, upon checking the condition of the skin from various points of view, it is possible to decide more objective diagnosis of the skin.

Next, there will be given an explanation about replica decision using impression agent that is another one of the skin analysis techniques. Here, this impression agent is raw material for copying shape of the skin.

This method is that the impression agent made from silicon rubber is made to apply to the customer's skin, for instance, on the skin of the cheek to copy minute irregularity of surface of the skin in which the copy of the skin is taken as replica, then the irregularities on the replica are classified into a plurality of stages by every category such as size of a texture of the skin, degree of abrasion of the texture, tension of the skin, size of pores, flow of the skin (directionality), or so forth while observing distribution of irregularities on this replica.

Figure 9:
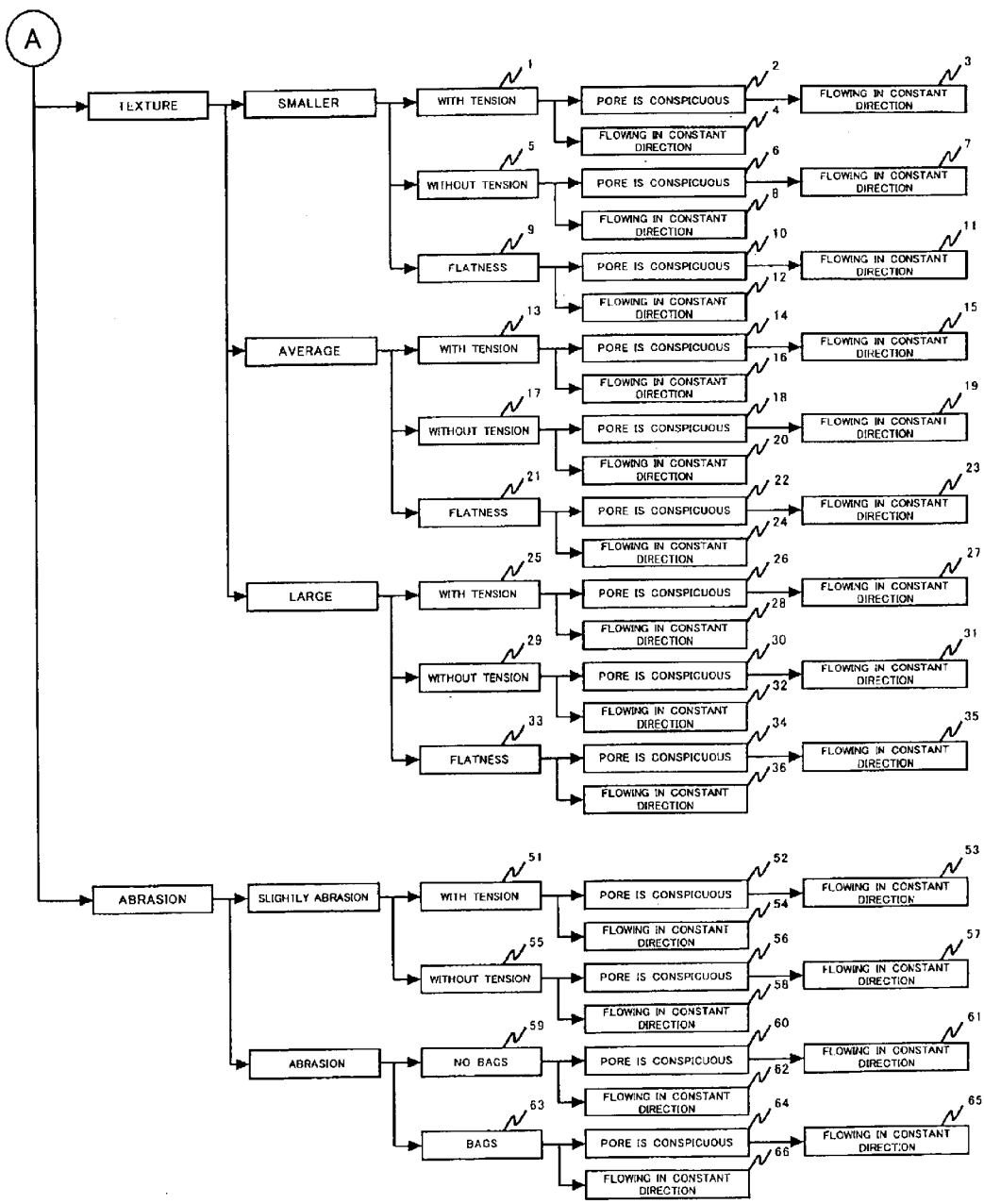
FIG. 9 is a diagram illustrating an exemplary tree of classification to be criterion of the skin according to the replica.
Figure 10:
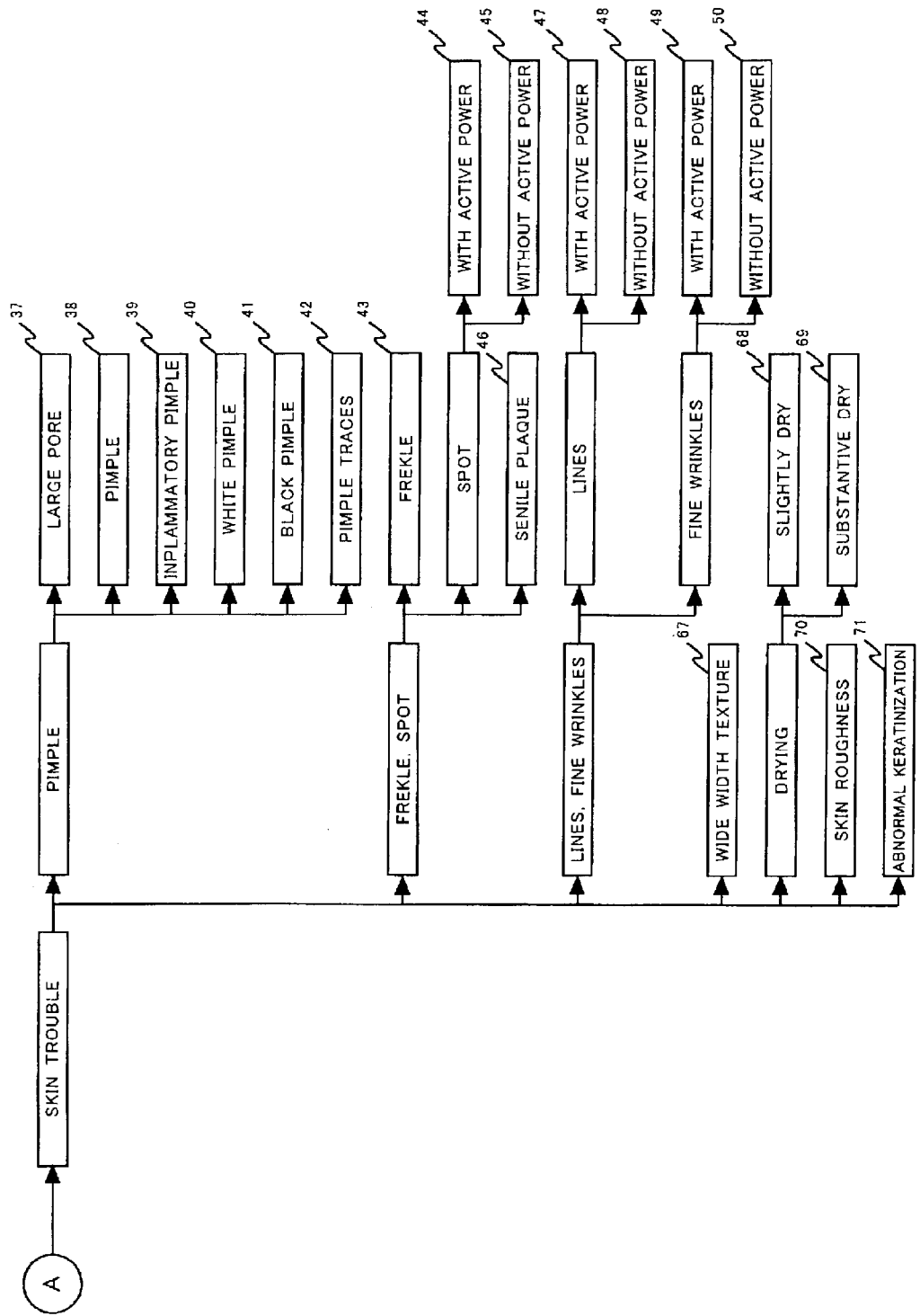
FIG. 10 is a diagram illustrating an exemplary tree of classification to be criterion of the skin according to the replica.

Further, in addition thereto, there are further classified points of view such as a skin eruption, a spot, lines, drying, skin roughness, trouble of keratin or so forth. FIGS. 9, and 10 illustrate an exemplary tree of classification to be criterion of judgment of the replica. In this tree of classification, there is classified the skin into 71 subsections.

Concretely, the impression agent with the silicon rubber as main body is applied to the skin wherein test piece provided with a window of 20 mm×20 mm is dabbed against the skin of the cheek under the eye so that the impression agent comes into contact with the skin, then the replica with the size of the window can be obtained while waiting for drying of the impression agent. Thereafter, this replica is made to image in such a way that light and shade is conspicuous. Based on a result of the imaging, longitudinal level, the height and the width based on the light and shade are quantized into the number of 256 respectively to input them into the computer, and then numerical data of a plurality of categories is obtained upon performing image processing, with the result that a decision is performed by this numerical data.

For instance, in analysis of the texture, the longitudinal level of the replica image is made to decide from luminance, wherein when scanning the replica image, the skin is delicate skin with increasing the number of peaks of the light and shade, or the skin is delicate skin as difference of the light and shade (difference of longitudinal level) is large.

The following numerical data are obtained by the image processing:

(1) The number of peaks of the texture;
(2) The number of the textures according to particle instrumentation of the texture;
(3) The number of particles at dark portion;
(4) The number of particles at bright portion;
(5) The average value of interval of the texture;
(6) The standard deviation of interval of the texture;
(7) The average value of the longitudinal level of the texture;
(8) The standard deviation of the longitudinal level of the texture;
(9) The area comparison based on difference of density;
(10) The standard deviation of orientation of the texture;
(11) The total (particle instrumentation) of size of the texture;
(12) The average (particle instrumentation) of size of the texture;
(13) The standard deviation (particle instrumentation) of size of the texture;
(14) The standard deviation (particle instrumentation) of brightness of dark particle;
(15) The standard deviation density value of the total images;
(16) The average (particle instrumentation) of brightness of bright particles;
or so forth.

According to these matters, for instance, decision whether or not there are textures is made in such a way that when there are more than 30 particles within the samples in "(2) The number of the textures based on particle instrumentation of the texture;", decision is that there are textures.

Decision of size of texture, namely, decision whether the skin is delicate skin or rough skin is capable of being performed in such a way that when the above described "(5) The average value of interval of the texture" is not more than 25 (1.95 mm) while quantizing 20 mm of the window into the number of 256, the skin is decided as the delicate skin, while when the above described "(5) The average value of interval of the texture" is more than 25 (1.95 mm) while quantizing 20 mm of the window into the number of 256, the skin is decided as the rough skin. Also, decision whether or not the skin is supple skin is capable of being performed whether or not there is dark portion on the skin hill within the texture.

Decision concerning the pore is one whether the pore is conspicuous or inconspicuous. Conspicuity of the pore is decided whether or not filled black hole is dispersed in the image When filled black holes more than four within the area of 3 mm×3 mm are dispersed, it is decided that the pore is conspicuous, while when filled black holes not more than four within the area of 3 mm×3 mm are dispersed, it is decided that the pore is inconspicuous.

Decision of flow of the skin is performed in such a way that when intension of the texture from upper left to lower right on the screen is clear, there is decided that flow of the skin from upper left to lower right exists, while when intension of the texture from upper right to lower left on the screen is clear, there is decided that flow of the skin from upper right to lower left exist.

Also, decision of the condition of the dry skin is performed in such a way that when the texture flows continuously, so that the texture cannot be confirmed sufficiently, it is decided that the skin is dry skin.

Further, ultimate conclusions are made to provide in such a way as to add analysis according to the computer to analysis according to the visual check. It should be noted that the part of trouble skin of FIG. 10 on the tree of classification is mainly the part of classification according to the visual check.

Figure 11:
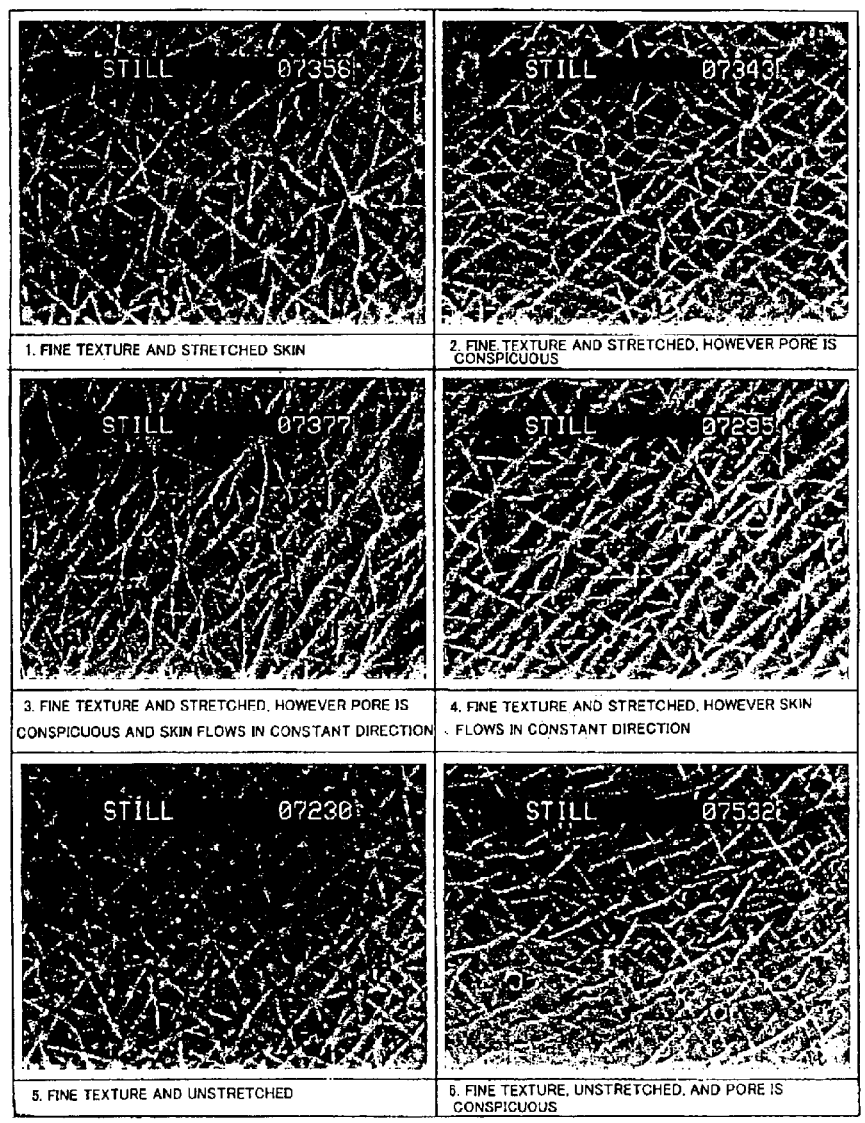
FIG. 11 is a diagram illustrating an exemplary result of decision of the skin in accordance with decision using replica.

It is possible to decide fundamental characteristic of the skin, current health condition, affection of the skin or so forth from these classifications. FIG. 11 illustrates an exemplary result of decision concerning the skin according to replica decision.

Next, there will be described about decision of information data within the keratin by the keratin checker for deciding health condition of horny cell that is another one of the skin analysis techniques.

The keratin checker is peculiar tape. The keratin checker is formed so that medicals of the tape absorb component within the keratin of the skin after the peculiar tape is made to attach on the skin under the eye and to press slowly after face washing.

The tape by which the component within the keratin is collected by this method is fed into the stain solution to stain for analyzing the component of the keratin. The result of the analysis is classified into, for instance, 9 subsections while separating the result of the analysis into a plurality of stages by every category such as size of the keratin, arranged state thereof or so forth. Further, there is added the existence of the nucleus within the cell to the classification of this subsection. It is possible to decide degree of health of keratin of the skin from these classifications. FIG. 12 illustrates an exemplary decision result of the skin according to the keratin analysis.

Figure 13:
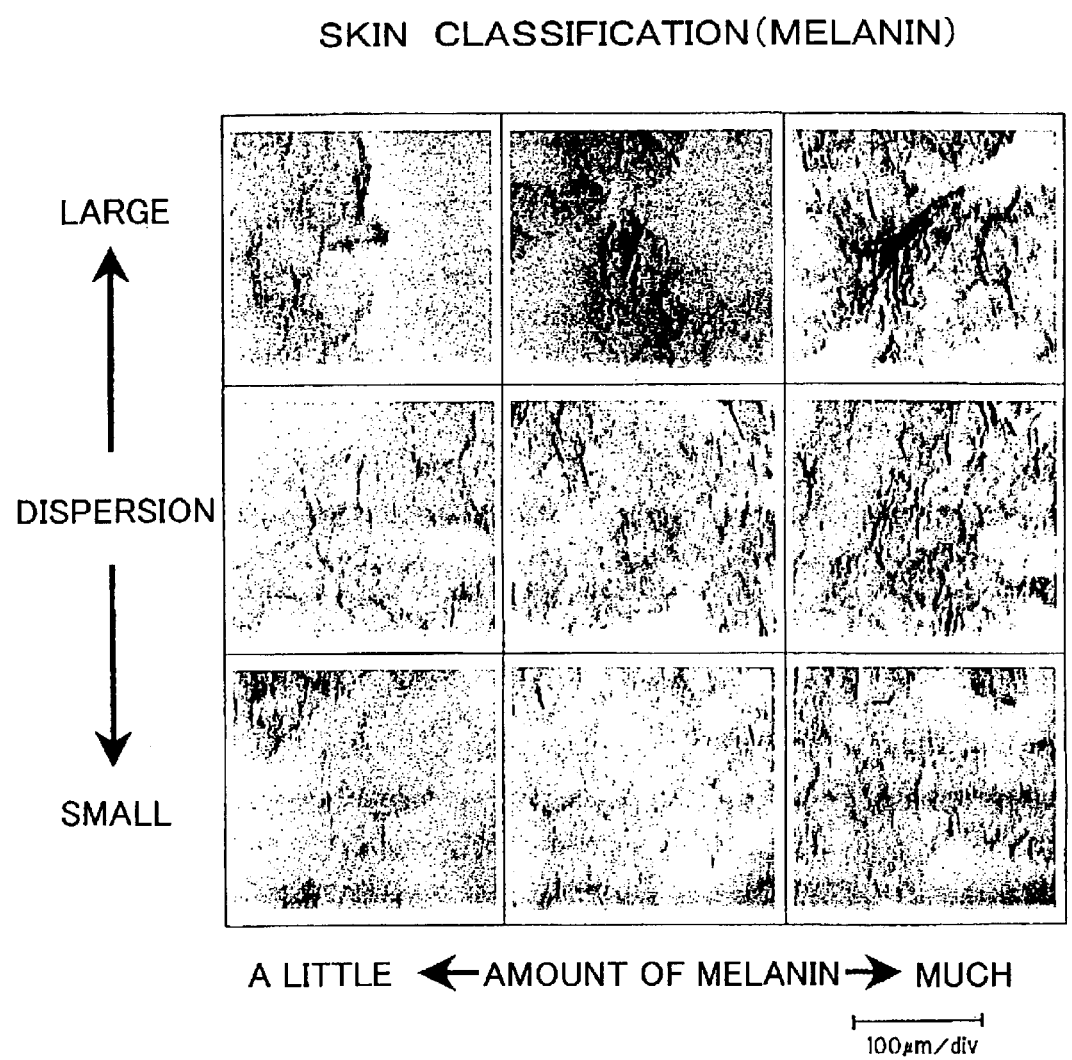
FIG. 13 is a diagram illustrating an exemplary result of decision of the skin in accordance with melanin analysis.

Next, there will be described about decision of melanin information data according to melanin checker for deciding health condition of the skin from the melanin pigment that is another one of the skin analysis techniques. The melanin checker as well as the keratin checker is peculiar tape. The melanin checker is formed so that medicals of the tape absorb melanin component within the skin after the peculiar tape is made to attach on the skin under the eye and to press slowly after face washing. The tape by which the melanin component is collected by this method is fed into the stain solution to stain for analyzing the melanin component of the skin. The result of the analysis is classified into, for instance, 9 subsections while separating the result of the analysis into a plurality of stages by every category such as amount of the melanin, dispersion of the melanin or so forth. It is possible to decide degree of health of the melanin of the skin from these classifications. FIG. 13 illustrates an exemplary decision result of the skin according to the melanin analysis.

Further, it is also possible to include the check of the flesh color in the above the skin analysis techniques. The check of the flesh color is that the customer compares color of the own skin with color of plural flesh color sheets before the customer designates the flesh color by color number of the flesh color sheets that is capable of being thought as the closest color to the own flesh color. According to this way, the flesh color of the customer can be classified.

It should be noted that the classified data of the flesh color can provide change of degree of the health of the skin upon comparing the classified data of the flesh color with the past data, and that the classified data of the flesh color is one of the important data especially to select cosmetics of the customer.

Figure 14:
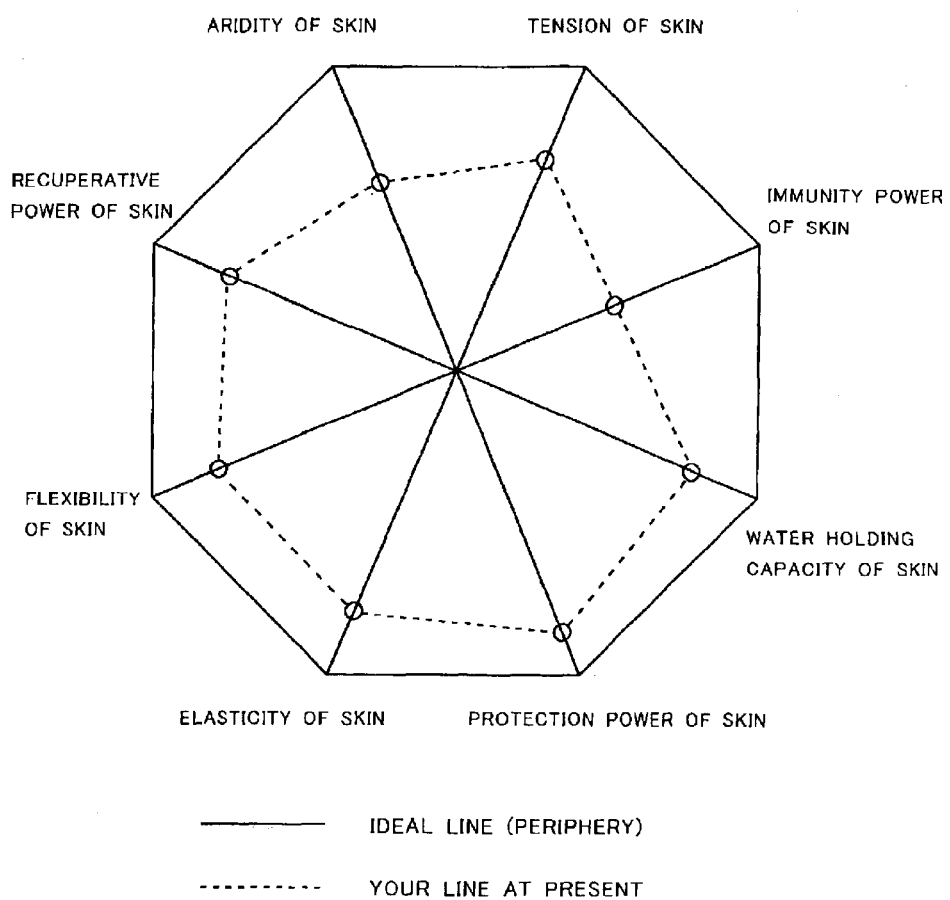
FIG. 14 is a diagram illustrating an exemplary chart indicating result of comprehensive decision of the skin.

Ultimately, upon performing comprehensive judgment based on results of each analysis described above, as illustrated in FIG. 14, points of view of tension of the skin, power of immunity of the skin, water holding capacity of the skin, power of protection of the skin, elasticity of the skin, flexibility of the skin, recuperative power of the skin and aridity of the skin are indicated on the chart. Then, comprehensive maintenance procedure and corrective strategy of the skin are decided from the chart to instruct and then the cosmetics for use in the maintenance procedure and the corrective strategy are recommended.

The foregoing description of the method for skin analysis according to preferred embodiments of the present invention has been provided for the purpose of illustration and description. It is not intended to be exhaustive or to limit the invention to the precise forms disclosed. Obviously, many practitioners skilled in the art. The embodiments were chosen and described in order to best explain the principles of the invention and its practical application, thereby enabling others skilled in the art to understand the invention for various embodiments and with various modifications as are suited to the particular use contemplated. For instance, in the description described above, there was described that the tree of classification of FIGS. 9 and 10 is made to use for decision of the replica of the skin. However, it is also possible to perform pattern matching processing between the replica of the skin and reference pattern stored beforehand in the computer. Also in the keratin checker or the melanin checker, it is possible to adopt decision using pattern matching similarly.

What is claimed is:

1. A method for analyzing the skin, the comprising:
   a. analyzing the skin to obtain analysis data of the skin of a customer based on a plurality of the skin analysis techniques;
   b. classifying conditions of the skin of the customer into a plurality of classifications based on said data; and
   c. diagnosing the condition of the skin of the customer in accordance with said classifications, and
   wherein analysis of data obtained by answers to an interview concerning conditions of the skin, nature of the skin and current maintenance procedures in terms of the customer is included as one of said plurality of skin analysis techniques.

2. A method for analyzing the skin, comprising:
   a. analyzing the skin to obtain analysis data on the skin of a customer based on a plurality of the skin analysis techniques;
   b. classifying conditions of the skin of the customer into a plurality of classifications based on said data; and c. diagnosing the condition of the skin of the customer in accordance with said classifications and, wherein image analysis of a replica by impression agent in which irregularities of the surface of the skin are copied is included as one of said plurality of skin analysis techniques.

3. A method for analyzing the skin, comprising:

a. analyzing the skin to obtain analysis data on the skin of a customer based on a plurality of skin analysis techniques;

b. classifying conditions of the skin of the customer into a plurality of classifications based on said data; and c. diagnosing the skin condition to diagnose condition of the skin of the customer in accordance with said classifications, and wherein analysis of data for keratin components obtained from the skin of the customer is included as one of said plurality of skin analysis techniques.

4. A method for analyzing skin, comprising:

a. analyzing the skin to obtain analysis data of the skin of a customer based on a plurality of the skin analysis techniques;

b. classifying conditions of the skin of the customer into a plurality of classifications based on said data; and c. diagnosing the condition of the skin of the customer in accordance with said classifications, and wherein analysis of data for melanin obtained from the skin of the customer for determining the condition of pigment of the skin is included as one of said plurality of skin analysis techniques.

5. The method for analyzing the skin according to any of claims 1 to 4, wherein said classification step employs classifications based on one or more of the condition of the skin, the nature of the skin, the texture of the skin, surface waviness of the skin, pore, direction of flow of groove, health condition, and current use condition of cosmetics.

6. The method for analyzing the skin according to any of claims 1,3 and 4, wherein said classification step employs pattern matching image processing in terms of database sample replica in which irregularities of the surface of the skin is copied.

* * * * *